United States Patent [19]

Furukawa et al.

[11] Patent Number: 5,032,410
[45] Date of Patent: Jul. 16, 1991

[54] FEED COMPOSITION FOR CULTURING FISHES

[75] Inventors: Tadayasu Furukawa, Chesterfield, Mo.; Noboru Takeno, Tokyo, Japan

[73] Assignee: Kyowa Hakko Kogyo Co., Ltd., Tokyo, Japan

[21] Appl. No.: 528,481

[22] Filed: May 25, 1990

[30] Foreign Application Priority Data

May 26, 1989 [JP] Japan .................. 1-133832

[51] Int. Cl.$^5$ .................. A23K 1/10
[52] U.S. Cl. .................. 426/2; 426/643; 426/646; 426/656; 426/657; 514/18; 514/893
[58] Field of Search .................. 426/2, 656, 657, 643, 426/646, 805; 514/893, 18

[56] References Cited

U.S. PATENT DOCUMENTS 4,870,071 9/1989 Ogata et al. .................. 514/893

FOREIGN PATENT DOCUMENTS 156349 8/1985 Japan .

OTHER PUBLICATIONS

Imada et al., "Use of Glutathione in Yellowtail Fish Nutrition Examined", Feedstuffs, Mar. 31, 1986, pp. 17 and 18.

*Primary Examiner*—R. B. Penland
*Attorney, Agent, or Firm*—Antonelli, Terry, Strout & Kraus

[57] ABSTRACT

Disclosed is a feed composition for culturing fishes, which comprises a peptide represented by the general formula (I):

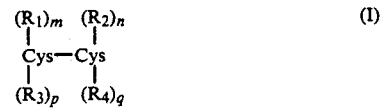

wherein Cys-Cys means a disulfide linkage of cysteinyls; each of $R_1$, $R_2$, $R_3$ and $R_4$ independently represents γ-L-glutamyl or glycyl; each of m,n,p and q is an integer of 0 or 1, provided that m,n,p and q are not simultaneosuly 0; and a conventionally formulated fish feed.

The peptide in the feed composition is effective in treating and preventing hepatic disorders of cultured fishes.

4 Claims, No Drawings

FEED COMPOSITION FOR CULTURING FISHES

BACKGROUND OF THE INVENTION

Aquaculture has been developing remarkably in recent years. In accordance therewith, deterioration in the freshness of such rich-haul fishes as sardine and mackerel, which are used as feed for cultured fishes, causes a serious problem in that cultured fishes suffer from hepatic disorders due to the high peroxylipid content in the deteriorated fish feed.

It is feared that the hepatic disorders will become aggravated and chronic under the stress of farming conditions. It is known that glutathione ($\gamma$-L-glutamyl-L-cysteinylglycine) is useful for the prevention and treatment of such hepatic disorders (Japanese Published Unexamined Patent Application No. 156349/1985).

Because glutathione, i.e., a thiol compound, is an unstable compound, it has an unsatisfactory effect when its use method is improper.

Even if it is properly used, glutathione is not sufficiently effective in the case of serious hepatic disorders. Under these circumstances, there has been a demand for the development of a compound which is stable and achieves satisfactory effects on serious hepatic disorders.

SUMMARY OF THE INVENTION

The present invention provides a feed composition for culturing fishes, which comprises a peptide represented by the general formula (I):

wherein Cys——Cys means a disulfide linkage of cysteinyls; each of $R_1$, $R_2$, $R_3$ and $R_4$ independently represents $\gamma$-L-glutamyl or glycyl; each of m,n,p and q is an integer of 0 or 1, provided that m,n,p and q are not simultaneously 0;
and a conventionally formulated fish feed. The present invention also provides a method of culturing fishes, which comprises culturing fishes in a conventional manner while having the fishes ingest the defined peptide, as well as a method of preventing and treating hepatic disorders of cultured fishes which comprises having the cultured fishes ingest the defined peptide.

DESCRIPTION OF THE INVENTION

Preferably, as the peptide to be used in the present invention, glutathione disulfide, $\gamma$-L-glutamyl-L-cystine and $\gamma$-L-glutamyl-L-cysteine disulfide are mentioned.

The structures of glutathione disulfide, $\gamma$-L-glutamyl-L-cystine and $\gamma$-L-glutamyl-L-cysteine disulfide are shown below. These peptides are found in living bodies and are very safe compounds for fishes. They are also very stable and are not decomposed when they are mixed with fish feed.

Glutathione disulfide

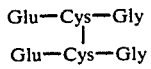

$\gamma$-L-Glutamyl-L-cystine

Glu—Cys—Cys $\gamma$-L-Glutamyl-L-cysteine disulfide

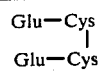

The peptide of the present invention includes a mixture of peptides represented by the general formula(I), and is easily synthesized in a conventional manner.

The amount of the peptide to be ingested by the cultured fishes is 1 to 1000 mg/kg per day. The peptide is admixed with raw materials of the artificial synthetic feed, or with a powdery raw material of the artificial synthetic feed, followed by mixing with other raw materials. Alternatively, the peptide may be admixed with chopped fish meat, or with a powdery raw material of the artificial synthetic feed, followed by mixing with chopped fish meat.

The amount of the peptide to be contained in the artificial synthetic feed, chopped fish meat and a mixture thereof is arbitrary. However, the peptide is preferably used in an amount of 0.01 to 5% by weight based on the artificial synthetic feed, chopped fish meat and a mixture thereof.

As the source of the artificial synthetic feed, the animal materials such as fish meal, case in and squid meal, the vegetable materials such as soybean oil meal, wheat flour, $\alpha$-starch and yeasts for feeds, the animal oils and fats such as cod-liver oil and squid-liver oil, the vegetable oils and fats such as soybean oil and rapeseed oil, vitamins, minerals, amino acids and antioxidizing agents are mentioned.

The fishes to be utilized for chopped fish meat include, for example, sardine, anchovy, mackerel, mackerel pike, Atka mackerel, herring, cod and sand launce.

The fishes to which the present invention is applicable include, for example, porgy, red sea bream, striped beakperch, flounder, righteyed flounder, yellowtail, striped jack, sweat fish, salmon, trout, Kuruma prawn and swimming crab.

The peptide of the present invention effectively suppresses the outbreak of hepatic disorders in cultured fishes caused by known fish feed and also remarkably treat hepatic diseases, thereby significantly reducing mortality.

The following examples will further illustrate the invention.

EXAMPLE 1

Glutathione disulfide, $\gamma$-L-glutamyl-L-cystine or $\gamma$-L-glutamyl-L-cysteine disulfide (20 grams each) was admixed with 100 kg of thawed frozen sardines. Each of the mixtures was minced with a meat chopper, giving the feed composition for culturing fishes.

EXAMPLE 2

To a feed composition composed of 53.5 kg of cuttle meal, 2 kg of a 1:1 mixture of arginine and methionine, 19 kg of feed yeast, 3 kg of $\alpha$-starch, 8 kg of mixed minerals (McCollum salt), 6 kg of vitamins mixture followed by Halver, 4 kg of fish liver oil and 3 kg of soybean lecithin, was added glutathione disulfide, $\gamma$-L-glutamyl-L cystine or $\gamma$-L-glutamyl-L-cysteine disulfide (0.1 kg each). 30 kg of water was further admixed therewith, and the resulting mixture was kneaded and molded by the use of an extruder (product of Wenger Inc.). The molded product was air-dried, giving the artificial synthetic feed.

EXAMPLE 3

500 individuals of yellowtail (average body weight: 500 g) were divided into five groups, each consisting of 100 individuals. The three test groups were fed the feed composition prepared in Example 1 once a day over a period of 15 days. The feed composition contains 0.02 weight % of glutathione disulfide, γ-L-glutamyl-L-cystine or γ-L-glutamyl-L-cysteine disulfide. The control groups were similarly fed the feed composition prepared in Example 1 except for the absence of the compound or the feed composition as prepared in Example 1 except for containing 0.02 weight % of glutathione in place of the compound.

Five individuals were picked at random from each group on the first day prior to the feeding of the feed composition and on the last day after the final feeding, and the enzyme activities of glutamic oxaloacetic transaminase (hereinafter referred to as GOT) and glutamic pyruvic transaminase (hereinafter referred to as GPT) in the blood were determined by Karmen method.

The results are shown in Table 1.

TABLE 1

| Feed Composition | GOT Value | | GPT Value | |
|---|---|---|---|---|
| | First day | Last day (15th day) | First day | Last day (15th day) |
| Control group | | | | |
| No additive | 55.3 ± 20.5 | 70.2 ± 45.6 | 29.2 ± 21.3 | 30.1 ± 19.4 |
| Glutathione | | 25.3 ± 10.4 | | 6.3 ± 0.7 |
| Test group | | | | |
| Glutathione disulfide | | 10.6 ± 8.6 | | 5.3 ± 0.4 |
| γ-L-Glutamyl-L-cystine | | 9.7 ± 7.3 | | 3.6 ± 0.3 |
| γ-L-Glutamyl-L-cysteine disulfide | | 10.1 ± 6.8 | | 4.7 ± 0.8 |

(Unit: Karmen Unit, each value represents the mean ± S.E.)

As is apparent from the table, the GOT and GPT enzyme activity values in the test groups where the feed composition of this invention prepared in Example 1 was fed, are remarkably lowered compared with those of the control groups. The feed compositions of the present invention have the excellent effect of enhancing the hepatic functions.

EXAMPLE 4

100 individuals of porgy (average body weight: 250 g) were divided into five groups, each consisting of 20 individuals. The three test groups were fed the feed composition prepared in Example 2 once a day over a period of 30 days. The feed composition contains 0.1 weight % of glutathione disulfide, γ-L-glutamyl-L-cystine or γ-L-glutamyl-L-cysteine disulfide. The control groups were similarly fed the feed composition prepared in Example 2 except for the absence of the compound or the feed composition as prepared in Example 2 except for containing 0.1 weight % of glutathione in place of the compound.

Five individuals were picked at random from each group on the first day prior to the feeding of the feed composition and on the last day after the final feeding, and the enzyme activities of GOT and GPT in the blood were determined by Karmen method.

The results are shown in Table 2.

TABLE 2

| Feed Composition | GOT Value | | GPT Value | |
|---|---|---|---|---|
| | First day | Last day (30th day) | First day | Last day (30th day) |
| Control group | | | | |
| No additive | 80.7 ± 46.3 | 72.6 ± 54.16 | 27.4 ± 26.9 | 33.2 ± 29.6 |
| Glutathione | | 48.7 ± 20.5 | | 22.7 ± 3.4 |
| Test group | | | | |
| Glutathione disulfide | | 11.3 ± 9.6 | | 6.2 ± 0.8 |
| γ-L-Glutamyl-L-cystine | | 9.9 ± 8.4 | | 5.5 ± 0.9 |
| γ-L-Glutamyl-L-cysteine disulfide | | 10.2 ± 5.8 | | 4.3 ± 1.0 |

(Unit: Karmen Unit, each value represents the mean ± S.E.)

As is apparent from the table, the GOT and GPT enzyme activity values in the test groups where the feed composition of this invention prepared in Example 2 was fed, are remarkably lowered than those of the control groups. The feed composition of the present invention has the excellent effect of enhancing the hepatic functions.

EXAMPLE 5

500 individuals of yellowtail (average body weight: 500 g) were divided into five groups, each consisting of 100 individuals. Frozen sardine meat was thawed chopped and exposed to sunlight for 3 hours to obtain a deteriorated feed. The deteriorated feed was fed to all the groups over a period of 15 days. During this period, no growth was observed in any group and about ten individuals per group were found dead. Thereafter, the feed composition of this invention prepared in Example 1 containing 0.02 weight % of glutathione disulfide, γ-L-glutamyl-L-cystine or γ-L-glutamyl-L-cystein disulfide was fed to the three test groups once a day over a period of 20 days. The control groups were similarly fed the feed composition prepared in Example 1 except for the absence of the compound or the feed composition prepared in Example 1 except for containing 0.02 weight % of glutathione in place of the compound.

Mortality of cultured fishes was counted over the entire period.

The results are shown in Table 3.

TABLE 3

| Feed Composition | Deteriorated feed | | Test feed | | | |
|---|---|---|---|---|---|---|
| | At the start | 15th day | At the start | 5th day | 10th day | 20th day |
| Control group | | | | | | |
| No additive | 100 | 75 | 75 (100) | 53 (71) | 40 (53) | 21 (28) |
| Glutathione | 100 | 74 | 74 (100) | 69 (93) | 64 (86) | 63 (85) |
| Test group | | | | | | |
| Glutathione disulfide | 100 | 76 | 76 (100) | 70 (92) | 68 (89) | 68 (89) |
| γ-L-Glutamyl-L-cystine | 100 | 75 | 75 (100) | 71 (95) | 67 (89) | 66 (88) |
| γ-L-Glutamyl-L- | 100 | 73 | 73 | 69 | 67 | 65 |

TABLE 3-continued

| Feed Composition | Deteriorated feed | | Test feed | | | |
| --- | --- | --- | --- | --- | --- | --- |
| | At the start | 15th day | At the start | 5th day | 10th day | 20th day |
| cysteine disulfide | | | (100) | (95) | (92) | (89) |

Value: the number of survivors;
( ): survival rate (%)

As is apparent from the table, the number of survivors, with respect to the test groups where the feed composition of this invention prepared in Example 1 was fed, is markedly larger than that of the control group where the feed composition containing no additive was fed, and is slightly larger than that of the group where the feed composition containing gluthathione was fed. That is to say, the feed composition of this invention is effective in treating the hepatic disorders caused by ingestion of deteriorated feed such as sardine feed exposed to sunlight.

What is claimed is:

1. A feed composition for culturing fishes and shellfishes, which consisting essentially of a peptide selected from the group consisting of glutathione disulfide, γ-L-glutamyl-L-cystine and γ-L-glutamyl-L-cystein disulfide and a conventionally formulated fish feed; the amount of the peptide being in a range of 0.01 to 5% by weight based on the conventionally formulated fish feed.

2. The feed composition according to claim 1, wherein the conventionally formulated fish feed is selected from the group consisting of an artificial synthetic feed, chopped fish meat and mixture thereof.

3. The feed composition according to claim 1, wherein the fishes and shellfishes are selected from the group consisting of porgy, red sea beam, striped beakperch, flounder, righteyed flounder, yellowtail, striped jack, sweat fish, salmon trout, Kuruma prawn and swimming crab.

4. A method of preventing or treating hepatic disorders of cultured fishes and shellfishes which comprises feeding the cultured fishes and shellfishes a conventionally formulated fish feed and a peptide selected from the group consisting of glutathione disulfide, γ-L-glutamyl-L-cystine and γ-L-glutamyl-L-cysteine disulfide in an amount of 1 to 1000 mg/kg per day based on the weight of the fish.

* * * * *